US006779905B1

(12) United States Patent
Mazursky et al.

(10) Patent No.: US 6,779,905 B1
(45) Date of Patent: Aug. 24, 2004

(54) ELECTRIC SENSORY DEVICE

(75) Inventors: Richard Mazursky, Riverwoods, IL (US); David Waskin, Niles, IL (US)

(73) Assignee: PDQ Mazoo, LLC, Riverwoods, IL (US)

( * ) Notice: Subject to any disclaimer, the term of this patent is extended or adjusted under 35 U.S.C. 154(b) by 75 days.

(21) Appl. No.: 09/941,111

(22) Filed: Aug. 28, 2001

Related U.S. Application Data

(60) Provisional application No. 60/295,044, filed on Jun. 1, 2001, and provisional application No. 60/262,190, filed on Jan. 17, 2001.

(51) Int. Cl.[7] ............................................. F21V 33/00
(52) U.S. Cl. ...................................... 362/101; 362/86
(58) Field of Search .......................... 362/86, 101, 253, 362/227, 251, 254

(56) References Cited

U.S. PATENT DOCUMENTS

| | | | | |
|---|---|---|---|---|
| 4,549,250 A | * | 10/1985 | Spector | 362/96 |
| 4,714,984 A | * | 12/1987 | Spector | 362/101 |
| 4,804,821 A | * | 2/1989 | Glucksman | 261/DIG. 89 |
| 5,111,477 A | * | 5/1992 | Muderlak et al. | 392/390 |
| 5,387,178 A | * | 2/1995 | Moses | 600/27 |
| 5,517,264 A | * | 5/1996 | Sutton | 353/119 |
| 5,574,821 A | * | 11/1996 | Babasade | 392/392 |
| 5,964,519 A | * | 10/1999 | Chun-Ying | 362/253 |
| 5,982,414 A | * | 11/1999 | Yoshida et al. | 348/552 |
| 6,000,658 A | * | 12/1999 | McCall, Jr. | 242/564.2 |
| 6,104,866 A | * | 8/2000 | DeWitt et al. | 392/390 |
| 6,478,440 B1 | * | 11/2002 | Jaworski et al. | 362/96 |
| 6,527,402 B1 | * | 3/2003 | Borri | 362/86 |

* cited by examiner

*Primary Examiner*—Thomas M. Sember
*Assistant Examiner*—Hargobind S. Sawhney
(74) *Attorney, Agent, or Firm*—Michael Best & Friedrich LLP

(57) ABSTRACT

The present invention relates to an apparatus and method for emitting light, sound and/or fragrance, which comprises a housing and means therein for connecting the apparatus to an electrical power source. A lighting system, sound system and fragrance system are mounted on or within the housing and are enabled simultaneously or individually by the electrical power source. The housing contains perforations, permeable membranes and/or translucent coverings on or in its walls to allow for the transmission of light, sound and fragrance when the apparatus is activated. The lighting system can be used as a direct light, nightlight, back light or a projected light, and the fragrance system utilizes various fragrances depending on the users desires. The sound system may contain a permanent sound chip or interchangeable sound cartridges, and the housing may have an almost limitless variety of desirable forms or designs and may contain interchangeable face plates to provide a wide variety of alternative decorative options. Because of the many decorative and functional options, the inventive apparatus can be made in different customized forms and located throughout the rooms of a house, with each customized apparatus being adapted to the specific room in which the apparatus is located in order to create a desired theme or environmental effect suitable for the particular room.

28 Claims, 5 Drawing Sheets

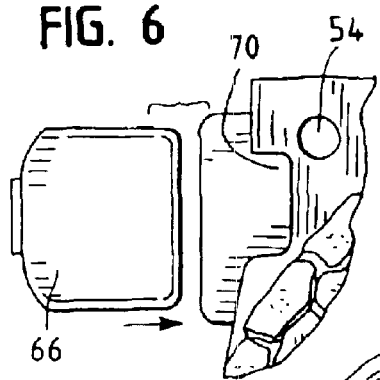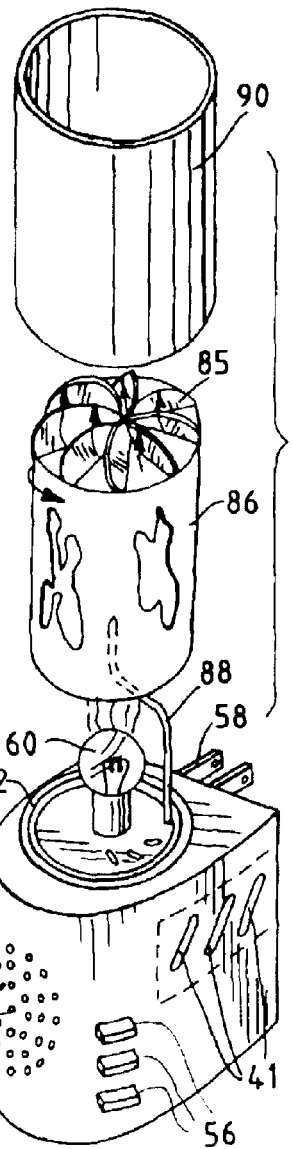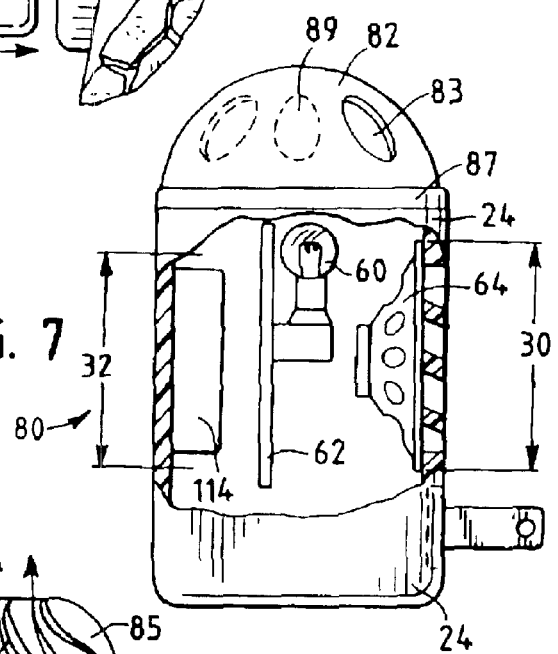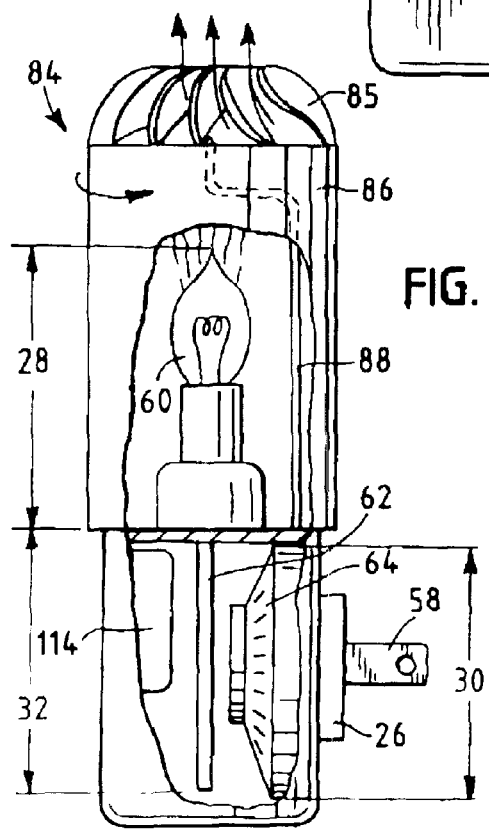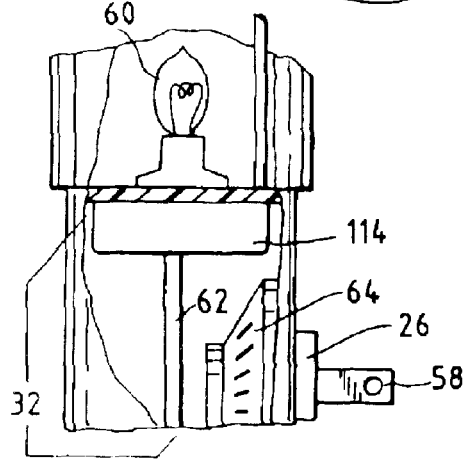

PDQ Mazoo

| Gym Room | Studio | Workshop |
|---|---|---|
| • N-Sync<br>• Rosewood | • Faith Hill<br>• Peppermint | • Ragtime<br>• Clove |

| Teenagers Room | Baby's Room | Bedroom |
|---|---|---|
| • Britney Spears<br>• Tangerine | • Lullabies<br>• Eucalyptus | • Nature sound<br>• Rose |

| Family Room | Living Room | Dining Room | Kitchen |
|---|---|---|---|
| • Big Band<br>• Rosemary | • Classical<br>• Lavender | • Strings<br>• Lemon | • Sinatra<br>• Cinnamon |

FIG. 11

ELECTRIC SENSORY DEVICE

Priority is claimed based on provisional applications Ser. No. 60/262,190, filed Jan. 17, 2001, and Ser. No. 60/295,044 filed Jun. 1, 2001.

FIELD OF THE INVENTION

This invention relates to a sensory apparatus and system and more particularly to an apparatus and system for emitting light, sound and/or fragrance.

BACKGROUND OF THE INVENTION

Consumers are continually seeking out small devices to enhance their lifestyles and personalize their homes. Thus, plug-in devices for emitting fragrance, for reducing household odors, or for emitting sound and light are known in the art. For example, one category of devices emits a fragrance into the surrounding area when connected to an electrical outlet. U.S. Pat. No. 5,647,053 discloses such a device, where a fragrant liquid is held within a container and vaporized into the surrounding area via the heat generated from an electrical heater. A light emitting device is shown in U.S. Pat. No. 4,912,609, which describes a conventional type night light that emits a low-level illumination to the surrounding area. U.S. Pat. Nos. 4,549,250 and 4,714,984 disclose night lights with a window to illuminate a picture, such as a flower. On the back of the picture is a fragrant pad containing a liquid that when heated by a light bulb contained within the device, vaporizes and is emitted into the surrounding area. U.S. Pat. No. 4,816,973 discloses a portable night light and air freshener that propels freshening media into the surrounding area via a rotating fan. U.S. Pat. No. 4,349,059 discloses a plug-in illuminating device combined together with a liquid fragrance container in a decorative housing. In this device, the light illuminates when connected to an electrical outlet and the fragrance is released when the user depresses a designated portion of the cover to aromatize the fragrant vapor into the surrounding area. Other light emitting devices are also known in the art. For example, U.S. Pat. No. 5,253,000 describes a plug-in device that projects images onto a wall or flat surface.

The prior art also includes devices for providing music or other sounds for babies that can be attached to a crib. For example, U.S. Pat. No. 5,991,131 discloses a crib light with a tape player. Others include crib lights and the use of sound recordings to provide soothing sounds. None of these sound and light devices appear to include a fragrance feature and all appear to be battery operated.

No plug-in device is known to applicant that combines light, fragrance, and sound in a single unit. Nor is applicant aware of a plug-in system that combines sound and fragrance. Thus, consumers currently searching for fragrance, light and sound emitting plug-in devices will at the very least have to purchase two separate devices in order to meet their needs. The present device conveniently packages, in one device, light, sound and fragrance features.

Thus, an object of this invention is to provide a plug-in system contained in a single unit that preferably emits fragrance, light and/or sound.

Another object of the invention is to provide a multifunction versatile sound, light and fragrance system that includes features and means for creating a wide variety of exterior decorative choices or appearances.

Yet another object of the invention is to provide multiple combinations of light, sound and/or fragrance systems in a single device to accommodate the different needs and desires of the user.

SUMMARY OF THE INVENTION

In keeping with one aspect of the invention, a device or an apparatus for emitting light, sound and fragrance is provided. The device contains a housing with perforations, permeable membranes and/or translucent coverings along its walls and/or body to allow for the transmission of light, sound and fragrance when the device is activated. The device includes a conventional plug for connecting it to a power source, which enables all three systems. This plug may be pivotable to allow the system to be used with vertical or horizontal electrical outlets. The light source is mounted in the housing and may include an incandescent or fluorescent bulb, or an electro-luminescence or light emitting diode (LED) and may function as a focused light, a backlight for a screen, or as a projected light.

The sound system is also mounted in the housing and Includes an audio speaker, an amplifier and means, such as a sound chip or cartridge which transmits prerecorded sound through the speaker to the surrounding area. The sound transmitting means is attached to a circuit board which in turn is connected to the amplifier and the speaker, all within the housing of the device. The sound transmitting means may be permanently attached to the circuit board or removable so that the user can interchange sound chips or cartridges. When an audio cartridge system is employed, the cartridges are interchangeable so that the user may vary sounds or music as desired. The cartridges are preferably insertable into a receptacle located within the housing and are preferably accessible to the user from outside the housing of the device.

The device includes a fragrance container that is adapted to be mounted on or within the housing. The fragrance may be contained in the receptacle in the form of a liquid mixture, saturated pads, beads, gel packs or a spray. An electrical warmer located within the housing provides heat necessary to cause the fragrance to vaporize. Alternatively, the light source may provide the necessary heat. The fragrant vapor is emitted to the surrounding area through perforations, vents or permeable membranes located on or in the walls of the housing.

System control switches may be provided to actuate independently each of the system components, and the system may include a timer to operate the device for predetermined time periods. Means may be provided to allow the user to control the amount of light, sound and/or fragrance emanating from the respective component. In this way, the user has greater control over the amount of light, sound or fragrance emitted from the system and device during use. A turbine may be attached to the housing, such that when the device is activated, the heat produced by the light source causes the turbine to rotate and project images on a translucent screen or into the surrounding area through a translucent screen. Where desired and appropriate, a battery, rather than typical AC power, may be used as the power source.

Also, a motion and/or light detector may be mounted within the housing with suitable means to detect movement or change in light brightness in order automatically to activate or shut off the system or various features of the system. Where desired, sensors may be included within the system for activating the device via an external remote control or transponder.

BRIEF DESCRIPTION OF THE DRAWINGS

FIG. 6 is a partial plan view of the embodiment of FIG. 1 illustrating the insertion of a sound cartridge into a holder;

FIG. 7 is a partial plan view of a second embodiment of the invention;

FIG. 8 is an exploded perspective view of another embodiment of the invention;

FIG. 9 is a partial plan view of the embodiment of FIG. 8 with an alternative arrangement for the fragrance system;

FIG. 10 is a partial plan view of the embodiment of FIG. 8, with the screen cover removed; and FIG. 11 is a schematic view of the rooms of a house illustrating the use of the system in the various rooms.

DETAILED DESCRIPTION OF THE PREFERRED EMBODIMENT

Figure 1:
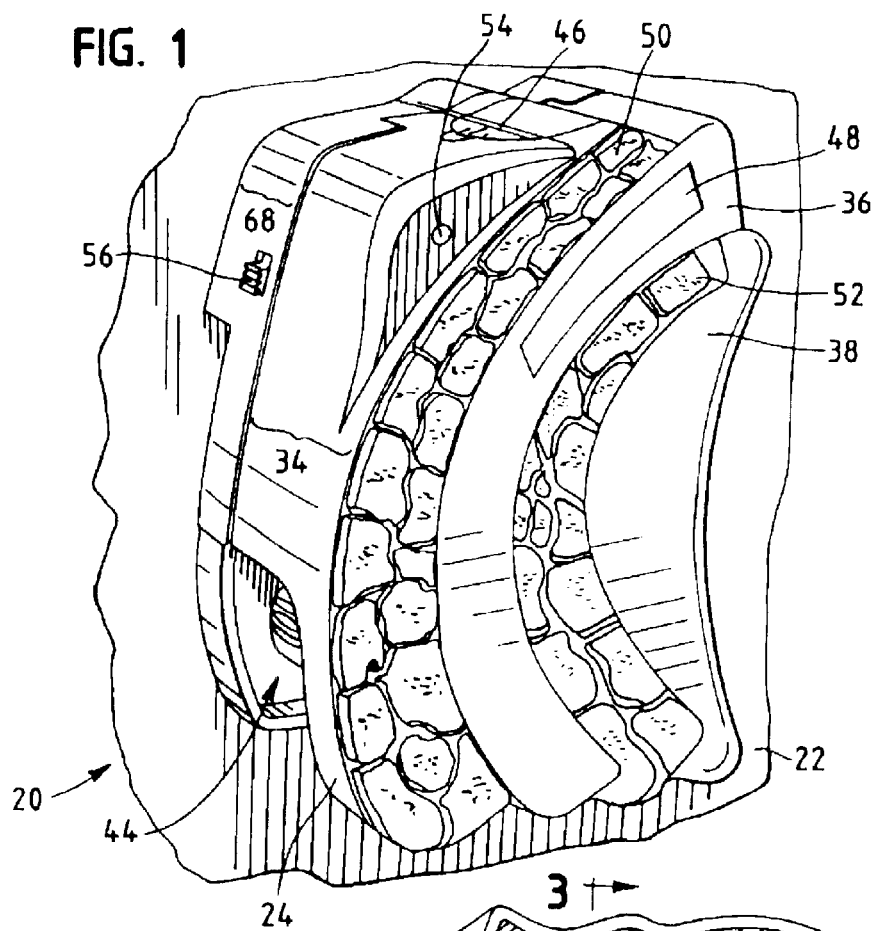
FIG. 1 is a front perspective view of one embodiment of this invention.
Figure 2:
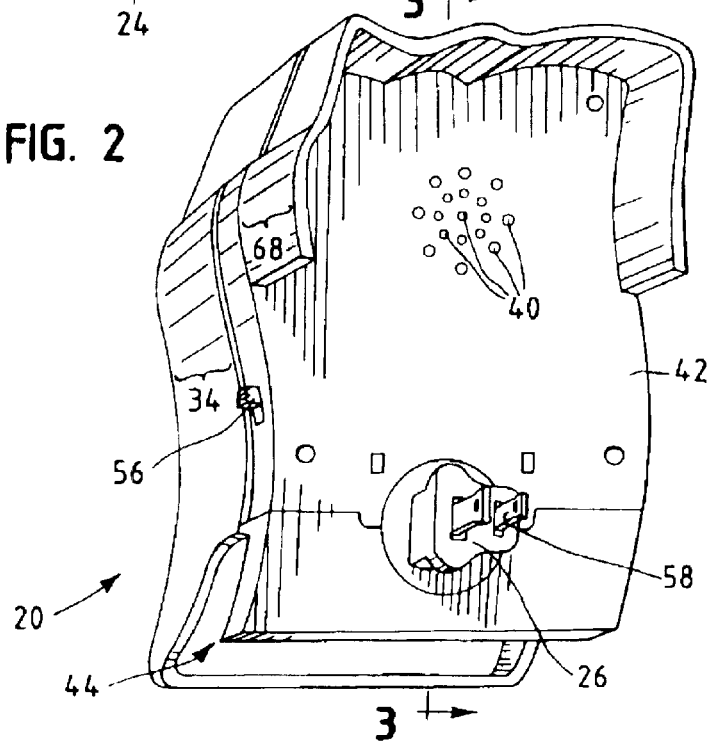
FIG. 2 is a perspective view of the back of the embodiment of FIG. 1.
Figure 3:
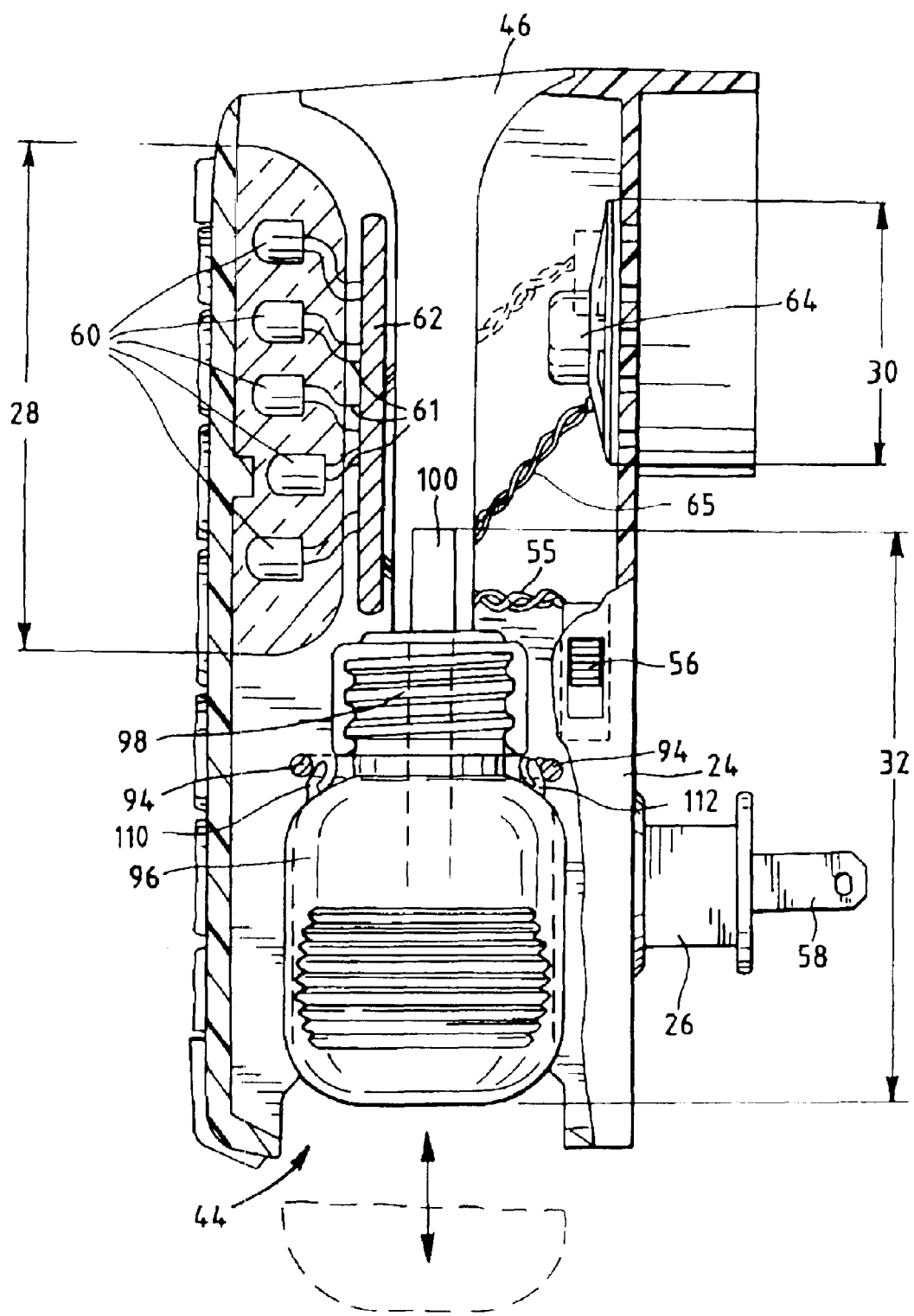
FIG. 3 is a cross section taken along line 3—3 of FIGS. 1 and 2.

Referring to the drawings, FIGS. 1 and 2 show the inventive device 20 capable of being plugged into an electrical outlet (not shown) on a wall 22. The device 20 consists of a housing 24 and a plug 26 (FIG. 2). The housing 24 contains a lighting system 28, a sound system 30 and a fragrance system 32, as illustrated in FIG. 3. The housing 24 further comprises a face plate 34 mounted thereon, which in the illustrated embodiment, resembles a stone wall and has translucent areas 36, 38 which transmit and diffuse light, a plurality of perforations 40 in the wall 42 of the housing 24, an opening 44 and a vent 46. The housing 24 may further contain a recessed area 48 that is adapted to contain images or other graphic designs.

Areas 50, 52 on the housing 24, may be frosted, opaque or perhaps a satin background designed to enhance a display of the translucent areas 36, 38 and the design used in the recessed area 48. An optical or infrared sensor 54 may be provided in the housing 24 to control the device 20 from a remote location. The remote controller (not shown) would transmit infrared light to the sensor 54, which then transmits signals to an electronic circuit that activates the device 20. The optical sensor 54 may also be designed to detect either movement in a room or a dimming of ambient light or both. This feature would be of interest when the device 20 is used as a night light to indicate when people are entering the proximity of the device. A switch 56 may be used to manually switch the device 20 on and off or to override the control signals produced via the optical sensor 54. The switch 56 may also be designed to operate independently for each of the functions of the device 20.

Referring to FIG. 2, the plug 26 includes contact blades 58, which may be rotatable so as to enable the device 20 to be mounted either horizontally or vertically to a wall outlet (not shown). The device 20 can be powered by a battery (not shown).

As shown in FIG. 3, the lighting system 28 consists of a light source 60 that can be mounted within the housing 24, as shown, or attached to the outside of the housing 24. The light source 60, which are illustrated as light-emitting diodes, is connected to the circuit board 62 through wiring 61. The light source 60 is located within the housing 24 adjacent to the translucent areas 36, 38, so that the emitted light flows through the areas 36, 38 to the surrounding area.

The light source 60 can include other means than light-emitting diodes, such as e.g. an incandescent lamp, and may emit a constant stream of light or a strobe as desired. As will be seen, the light source 60 may also serve to project images on the device or to the surrounding area and serve as a heat source for the fragrance emission.

The sound system 30 shown in FIG. 3, comprises a circuit board 62, at least one sound chip (not shown), an amplifier (not shown) and a speaker 64. The circuit board 62 is mounted in the housing 24 and electrically connected through wirng 55 to the switch 56, which in turn is connected to the plug 26. The sound chip mounted on the circuit board 62 is electrically connected to the speaker 64 through wiring 65. A generally U-shaped member 68 extends outwardly from the back part of the housing 24 (FIG. 2). Member 68 acts as a spacer when the device 20 is plugged into a wall outlet and provides an open area for sound waves to escape from the space created by member 68 and the back of the housing 24. Member 68 also helps to stabilize the device 20 when it is plugged into a wall outlet and provides a more attractive appearance to the device.

Figure 4:
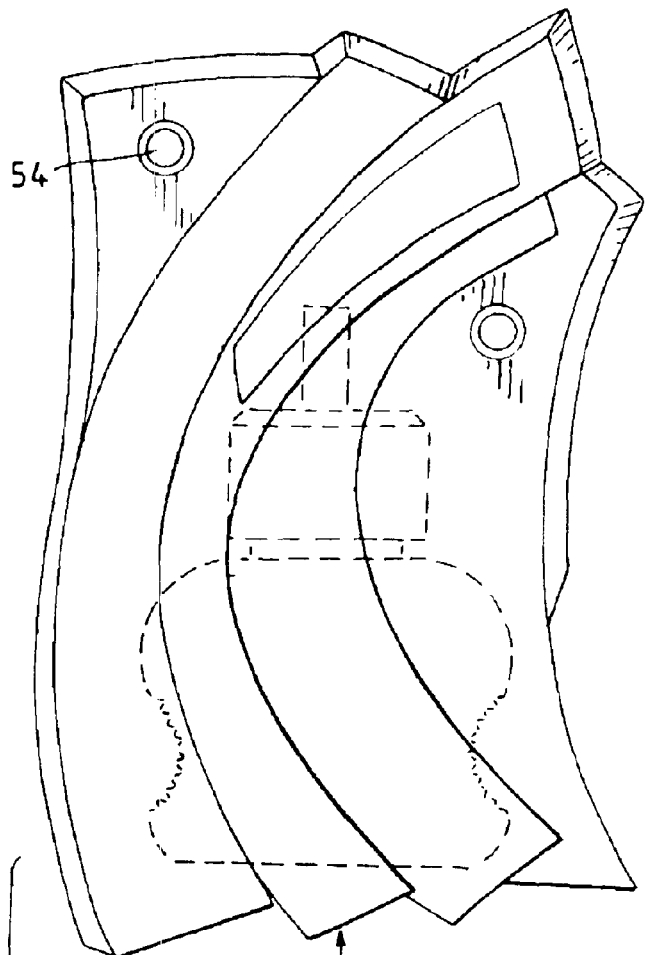
FIG. 4 is a partially exploded side elevational view of the embodiment of FIG. 1.

As shown in FIGS. 3 and 4, the fragrance system 32 consists of a warmer 94 and a container 96 with a neck 98 and a wick 100. The warmer 94 is a self-activating system contained within the housing 24 that encircles the neck 98 when the container 96 is inserted into the housing 24. The container 96 is removably attached to the housing 24 and contains a liquid fragrance. In this embodiment, the wick 100 extends into the liquid fragrance in order to draw the fragrance from inside the container 96 to be vaporized by heat from the warmer 94. The wick 100 continues upward through the container 96 and out the neck 98. The neck 98 of the container 96 is threaded so that a cap 102 (FIG. 4) may close it when not in use.

Figure 5:
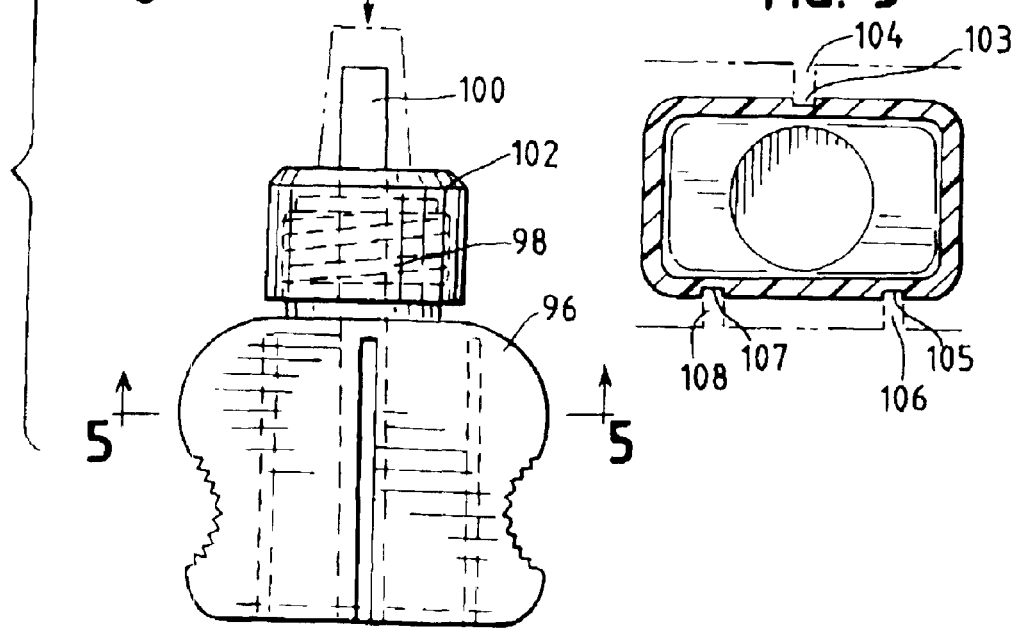
FIG. 5 is a cross section taken along line 5—5 of FIG. 4.

When a fragrance is desired, the container 96 is inserted into the opening 44 in the housing 24. To assist the insertion and retention of the container 96, a passage (not shown) lies adjacent to the opening 44 (FIG. 3). In positioning the container 96, the passage has vertically extending guides 104, 106, 108 (FIG. 5) molded in its sidewalls. The container 96 contains groves 103, 105, 107, shown in FIG. 5, that cooperate with the guides 104, 106, 108 to aid in holding the container 96 in the housing 24 during operation. Flexible fingers 110, 112 attached to the housing 24 contact the neck 98 to further aid in the retention of the container 96.

When the user inserts the plug 26 into an electrical power source (not shown), electric current flows through the device 20 and activates the lighting system 28, the sound system 30 and the fragrance system 32, simultaneously. In the lighting system 28, electric current powers the light source 60 and light is emitted through the translucent areas 36, 38 into the surrounding area. If the light source 60 is attached to the external portion of the housing 24, light will be emitted directly to the surrounding area without the need to pass through the translucent areas 36, 38. Simultaneously with activation of the light system, the circuit board 62 of the sound system 30 is electrically activated causing the sound chip to transmit electrical data to the speaker 64. The speaker 64 then transmits the data as sound through the perforations 40 to the surrounding area. Similarly, in an alternative embodiment shown in FIG. 6, the user may insert a separate sound cartridge 66 into the receptacle 70 of the housing 24 in lieu of the sound chip in device 20. This embodiment permits the user to interchange sound cartridges 66 as desired. Preferably, the system should be designed to permit the cartridge 66 to be inserted into the receptacle 70, so that the cartridge label is visible to the consumer even when the cartridge 66 is mounted in the device 20.

Together with the light and sound system, the warmer 94 of the fragrance system 32 is activated, causing it to produce and radiate heat. When the container 96 is inserted into the opening 44, the wick 100 is exposed to the warmer 94, and the heat radiating from the warmer 94 vaporizes the oil on the wick 100. The vapor escapes through the vent 46 in the wall or top portion of the housing 24 and is emitted to the surrounding area (FIG. 3). If desired, the light source may be used as the warmer for the fragrance system 32.

FIG. 7 shows an alternative embodiment 80, which additionally includes an outer dome 82 with at least one window 83 which may be clear, tinted or contain an image for projection. The dome 82 lies adjacent to the housing 24 and a wheel 87. An inner dome 89 rests inside the outer dome 82 and contains a translucent film (not shown) that may contain graphics or other images. The inner dome 89 is connected to the wheel 87 such that when the wheel 87 is turned, the inner dome 89 rotates with the wheel 87. As the inner dome 89 rotates, the images contained on the film pass beneath the window 83, such that when the light source 60 is activated the images are projected into the surrounding area. Additional windows 83 may be added.

In this embodiment, the fragrance system 32 consists of a gel pack 114 and heating element (not shown). When the system 32 is activated, the heating element warms the gel pack 114 causing it to release fragrant vapor into the surrounding area. Simultaneously, the light source 60 transmits light through the image window 83 within the dome 80 and projects the images into the proximate area. The sound system 30 transmits sound, as described in the previous embodiments.

FIG. 8 shows a further embodiment 84 including turbine 85, a translucent screen 86, and a light source 60. The screen 86 fits over the light source 60 and rests in a groove (not shown) on the housing. The screen 86 is made of a translucent or transparent material and may contain various images for projection. The turbine 85, connected to and positioned above the screen 86, balances on a rod 88, which extends the length of the screen 86. The heat produced from the light source 60 causes the turbine 85 and screen 86 to rotate, illuminating the images contained on the translucent screen 86 and in some instances projects the images to the surrounding area.

FIG. 8 contains a similar fragrance system 32 as shown in FIG. 7. However, when the lighting system 28 is activated in this embodiment, the light source 60 generates sufficient heat to cause the turbine 85 to rotate. As the turbine 85 rotates, images contained on screen 86 are illuminated or projected to the surrounding area. Similarly, FIG. 9 illustrates an alternative arrangement of the device, with the fragrance system 32 disposed adjacent to the light source 60.

Similarly, FIG. 10 contains a turbine 85, rod 88 and translucent screen 86. However, in this embodiment a removable transparent shade 90 is mounted over screen 86 and rests in a groove 92 around the light source 60. The turbine 85 is connected to the screen 86, which rotates with the turbine 85 while the shade 90 remains stationary. When the light source 60 is activated, the heat produced causes the turbine 85 to rotate. Images contained on the rotating screen 86 are projected onto the shade 90 and cause the images to appear to move across the shade 90. Individual switches 56 may be employed to actuate the lighting, sound and fragrance systems individually. Perforations 40 in the housing 24 provide an outlet for sound and vents 41, provide outlets for the fragrance.

Devices can be designed for use in some or all rooms of a house. This is illustrated in FIG. 11. Each room could employ its own device to emit appropriate sound, fragrance and light to accommodate the function of that room. If the device is intended for a baby's room, for example, the recessed area 48 could contain a moon design, which dimly glows, with the sound system playing lullabies to lull the baby to sleep and a soothing eucalyptus fragrance emitted from the fragrance system. Similarly, if the device is intended for a dining room, a soft light may be employed, with classical music and a light fragrance conducive to an eating environment. Placed in a teenager's room, the device may project moving images on the walls of a room while playing rock music and emitting a playful tangerine fragrance. Any number of other themes could be employed, depending on the intended use of the device, as illustrated, for example, in FIG. 11.

It will be understood that, in some instances, modifications of the system may be made without departing from the spirit and scope of the invention. For example, the sound and fragrance features may be combined without the lighting function. Likewise, other combinations of two or more of the systems of the invention may be appropriate. Also, other modifications of the invention will be evident to a person with skill in the art. It is the intention of the following claims to include such modifications.

What is claimed is:

1. An apparatus for emitting light, sound and fragrance comprising:
   a housing;
   a plug including contact blades, the contact blades being rigidly mounted with respect to the housing so that when the contact blades are inserted into an electrical wall socket, the plug mechanically supports the apparatus;
   a lighting system, a sound system and a fragrance system, each of the systems disposed in or on the housing;
   a rheostat for adjusting one or more of the lighting, sound, and fragrance systems, the rheostat being included in the housing;
   means for energizing the systems;
   wherein the lighting system comprises a light source;
   wherein the sound system comprises a circuit board, at least one sound chip, an amplifier and a speaker; and
   wherein the fragrance is obtained from a gel pack and the fragrance system comprises means for containing and dispensing the fragrance to the surrounding area.

2. The apparatus of claim 1, wherein the lighting, sound and fragrance systems are activated simultaneously by the electrical power source.

3. The apparatus of claim 1, wherein the energizing means is at least one electrical switch.

4. The apparatus of claim 1, wherein the energizing means is capable of operating each system independently of the other.

5. The apparatus of claim 1, wherein the fragrance dispensing means comprises a light source capable of generating sufficient heat to vaporize the fragrance.

6. The apparatus of claim 1, wherein the sound chip is permanently mounted on the circuit board.

7. The apparatus of claim 1, wherein a timing mechanism is provided to actuate and deactuate at least one of the systems.

8. The apparatus of claim 1, wherein the housing contains perforations or a semi-permeable membrane, which permits light to be transmitted from inside the apparatus to the surrounding area outside the apparatus.

9. An apparatus for emitting at least two components of the group including a light component, a sound component and a fragrance component, wherein the light component includes one or more of the group consisting of an incandescent bulb, fluorescent bulb, electro-luminescence, or light emitting diodes; the sound component includes a circuit board, at least one sound chip, an amplifier and a speaker, and the fragrance component includes means for containing and dispensing fragrance to the area surrounding the apparatus and means for heating the fragrance to generate sufficient heat to vaporize it;

wherein the fragrance system comprises a warmer and a receptacle having a neck, wick and liquid fragrance; and wherein the housing contains an opening to accommodate the receptacle, and the opening and the receptacle have cooperating connectors that interconnect to retain the receptacle in the housing during use and operation of the apparatus.

10. An apparatus for emitting light, sound and fragrance comprising:

a housing;

a plug including contact blades, the contact blades being rigidly mounted with respect to the housing so that when the contact blades are inserted into an electrical wall socket, the plug mechanically supports the apparatus;

a lighting system, a sound system and a fragrance system, each of the systems disposed in or on the housing;

a rheostat for adjusting one or more of the lighting, sound, and fragrance systems, the rheostat being included in the housing;

means for energizing the systems;

wherein the lighting system comprises a light source;

wherein the sound system comprises a circuit board, at least one sound chip, an amplifier and a speaker;

wherein the fragrance system comprises means for containing and dispensing fragrance to the surrounding area; and wherein an interchangeable face plate is attached to the housing.

11. The apparatus of claim 10, wherein the faceplate contains translucent or transparent areas to allow the passage of light from the light source within the housing to the surrounding area outside the housing.

12. The apparatus of claim 11, wherein the faceplate contains a recessed area that is illuminated by the light source.

13. The apparatus of claim 12, wherein the recessed area is covered by a design or graphic image.

14. An apparatus for emitting light, sound and fragrance comprising:

a housing;

a plug including contact blades, the contact blades being rigidly mounted with respect to the housing so that when the contact blades are inserted into an electrical wall socket, the plug mechanically supports the apparatus;

a lighting system, a sound system and a fragrance system, each of the systems disposed in or on the housing;

means for energizing the systems;

wherein the lighting system comprises a light source;

wherein the sound system comprises a circuit board, at least one sound chip, an amplifier and a speaker; and wherein the fragrance system comprises a warmer and a receptacle having a neck, wick and liquid fragrance, wherein the housing contains an opening to accommodate the receptacle, and the opening and receptacle have cooperating connectors that interconnect to retain the receptacle in the housing during use and operation of the apparatus.

15. The apparatus of claim 14, wherein the lighting system functions as a focused light, back light or a projection source.

16. The apparatus of claim 14, wherein the housing contains an area to receive the receptacle, and the receiving area and the receptacle have cooperating connectors that interconnect to retain the receptacle in the housing during use and operation of the apparatus.

17. The apparatus of claim 16, wherein the housing contains flexible projections to engage and retain the receptacle within the housing.

18. The apparatus of claim 14, wherein the sound chip is an interchangeable cartridge, a holder is provided for the cartridge, and the cartridge is releasably insertable into the holder.

19. The apparatus of claim 14, wherein a control circuit is mounted on the circuit board that controls the lighting, sound and fragrance systems.

20. An apparatus for emitting light, sound and fragrance comprising:

a housing;

a lighting system, a sound system and a fragrance system, each of the systems disposed in or on the housing;

a rheostat for adjusting one or more of the lighting, sound, and fragrance systems, the rheostat being included in the housing;

means for energizing the systems;

wherein the lighting system comprises a light source;

wherein the sound system comprises a circuit board, at least one sound chip, an amplifier and a speaker, the sound chip being an interchangeable cartridge having a holder, and the cartridge being releasably insertable into the holder; and wherein the fragrance system comprises means for containing and dispensing fragrance to the surrounding area.

21. An apparatus for emitting light, sound and fragrance comprising:

a housing;

a lighting system, a sound system and a fragrance system, each of the systems disposed in or on the housing;

a rheostat for adjusting one or more of the lighting, sound, and fragrance systems, the rheostat being included in the housing;

an optical sensor for detecting movement or changes in light intensity in the area surrounding the apparatus and actuating the apparatus when such movement or light change is sensed;

means for energizing the systems;

wherein the lighting system comprises a light source;

wherein the sound system comprises a circuit board, at least one sound chip, an amplifier and a speaker; and wherein the fragrance system comprises means for containing and dispensing fragrance to the surrounding area.

22. The apparatus of claim 21, wherein the light source is a strobe light.

23. The apparatus of claim 21, wherein the light source is an incandescent bulb, fluorescent bulb, electro-luminescence or light-emitting diodes.

24. The apparatus of claim 21, wherein the fragrance is obtained from a gel pack.

25. The apparatus of claim. 21, wherein a plug is provided to connect to an electrical outlet and rotates to accommodate horizontal or vertical electrical outlet.

26. The apparatus of claim 21, wherein means are provided for remotely actuating and deactuating the apparatus.

27. The apparatus of claim 21, wherein the housing contains a venting means for emitting fragrance from the system to the surrounding area outside the apparatus.

28. An apparatus for emitting light, sound and fragrance comprising:

a housing;

a lighting system, a sound system and a fragrance system, each of the systems disposed in or on the housing;

a rheostat for adjusting one or more of the lighting, sound, and fragrance systems, the rheostat being included in the housing;

means for energizing the systems;

wherein the lighting system comprises a light source;

wherein the sound system comprises a circuit board, at least one sound chip, an amplifier and a speaker; and wherein the fragrance system comprises means for containing and dispensing fragrance to the surrounding area.

* * * * *